(12) United States Patent
Bonny

(10) Patent No.: US 7,033,597 B2
(45) Date of Patent: Apr. 25, 2006

(54) INTRACELLULAR DELIVERY OF BIOLOGICAL EFFECTORS

(75) Inventor: Christophe Bonny, Morges (CH)

(73) Assignee: Université de Lausanne, Lausanne (CH)

( * ) Notice: Subject to any disclaimer, the term of this patent is extended or adjusted under 35 U.S.C. 154(b) by 510 days.

(21) Appl. No.: 10/165,015

(22) Filed: Jun. 7, 2002

(65) Prior Publication Data

US 2003/0032594 A1    Feb. 13, 2003

Related U.S. Application Data

(63) Continuation-in-part of application No. 09/977,831, filed on Oct. 15, 2001.

(60) Provisional application No. 60/240,315, filed on Oct. 13, 2000.

(51) Int. Cl.
*A61K 47/00* (2006.01)
*C07K 4/00* (2006.01)
*C12P 21/06* (2006.01)

(52) U.S. Cl. .................. 424/278.1; 514/2; 530/300; 530/326; 530/327; 530/810; 435/69.1; 435/320.1

(58) Field of Classification Search ............. 424/278.1; 530/300, 326, 327, 810; 435/69.1, 320.1; 514/2
See application file for complete search history.

(56) References Cited

FOREIGN PATENT DOCUMENTS

| CA | 2094658 | 4/1993 |
|---|---|---|
| FR | 2 767 323 | 2/1999 |
| WO | WO 94/23751 | 10/1994 |
| WO | WO 98/51325 | 11/1998 |
| WO | WO 98/51825 | 11/1998 |
| WO | WO 99/07414 | 2/1999 |
| WO | WO 00/12587 | 3/2000 |
| WO | WO 01/64738 | 9/2001 |
| WO | WO 02/31109 A2 | 4/2002 |

OTHER PUBLICATIONS

Anderson (1989). *Clin. Immun. and Immunopathol. 53*: S63-S71.
Ammendrup, et al. (2000). *Diabetes 49* 1468-1476.
Bleich, et al. (1999). *J. Clin. Invest. 103*(10): 1431-1436.
Bonner-Weir (1994) *Recent Prog. Hormone Res. 49*: 91-104.
Bonny, et al. (2001). *Diabetes 50*: 77-82.
Breeman, et al. (1999). *Int. J. Cancer 81*: 658-665.
Brugidou, et al. (1995). *Biochem. Biophys. Res. Commun. 214*(2): 685-693.
Burns, et al. (1998) *J. Biol. Chem. 273*(20): 12203-12209.

(Continued)

*Primary Examiner*—Padmashri Ponnaluri
(74) *Attorney, Agent, or Firm*—Ivor R. Elrifi, Esq.; Mintz, Levin, Cohn, Ferris, Glovsky and Popeo, P.C.

(57) ABSTRACT

The invention relates to sequences of amino acids with the capacity to facilitate transport of an effector across a biological membrane. More specifically, the present invention relates to novel peptide transporters that specifically target certain cell types for the intracellular delivery of drugs and therapeutic agents.

13 Claims, 2 Drawing Sheets

OTHER PUBLICATIONS

Chen, et al. (2000). *Diabetes 49*: 562-570.
Dupraz, et al. (1999). *Gene Therapy 6*: 1160-1169.
Efrat, et al. (1988). *Proc. Natl. Acad. Sci. USA 85*: 9037-9041.
Flodstrom, et al. (1999). *Diabetes 48*: 706-713.
Giannoukakis, et al. (1999). *Diabetes 48*: 1730-1736.
Gibbs (2000). *Science 287*: 1969-1973.
Gibbs and Oliff (1994). *Cell 79*: 193-198.
Hofland, et al. (1999). *Proc. Assoc. Am. Physicians 111*(1): 63-69.
Ivanenkov, et al. (1999). *Biochem. Biophys. Acta 1448*: 463-472.
Ivanenkov. et al. (1999). *Biochem. Biophys. Acta 1448*: 450-462.
Cabibbo, et al. (1995). *Gene 167*: 41-47.
Iwahashi, et al. (1996). *Diabetologia 39*: 530-536.
Iwahashi, et al. (1998). *Cytokines, Cell Mol. Ther. 4*: 45-51.
de Jong, et al. (1999). *J. Nucl. Med. 40*: 2081-2087.
Kato and Sugiyama (1997). *Critical Rev Thera. Drug Carr. Systems 14*(3): 287-331.
Kim, et al. (2000). *Anticancer Res. 20*: 439-444.
Larsen, et al. (1998). *J. Biol. Chem. 273*(24) 15294-15300.
Lin, et al. (1995). *J. Biol. Chem. 270*(24) 14255-14258.
Lund, et al. (1990). *J. Biol. Chem. 265*(25): 15713-15723.
Mahato, et al. (1997). *Critical Rev. Thera Drug Carr Systems 14*(2): 133-172.
Mahato, et al. (1997). *J. Drug Targeting 4*(6): 337-357.
Mandrup-Poulsen (1996). *Diabetologia 39* 1005-1029.
Mandrup-Poulsen (1998). *BMJ 316*: 1221-1225.
Mukherjee, et al. (1997). *Physiol. Rev. 77*(3): 759-803.
Negri, et al. (2000). *Genomics 64*: 324-330.
Nerup, et al. (1988). *Diabetes Care 11*(supp. 1): 16-23.
Oehlke, et al. (1998). *Biochem. Biophys. Acta 1414*: 127-139.
Offord, et al. (1997). *Meth. Enzymol. 287* 348-369.
Pasqualini and Ruoslahti (1996). *Mol. Psychiatry 1*: 423.
Peralta, et al. (1990). *Endocrinol. 127*(2): 595-603.
Rabinovitch, et al. (1999). *Diabetes 48* 1223-1229.
Renschler, et al (1994). *Proc. Natl. Acad. Sci USA 91*: 3623-3627.
Roitt (1991). *Essential Immunology*. Chapter 4: 65-83.
Rose and Vizzavona (1999) *J. Am. Chem Soc. 121*: 7034-7038.
Rouquet, et al. (1996). *Curr. Biol. 6*(9): 1192-1195.
Scharfmann and Czernichow (1996). *Diabetes and Metabolism 22*: 223-228.
Schwarze, et al. (1999). *Science 285*: 1569-1572.
Scott and Smith (1990). *Science 249*: 386-390.
Sjoholm (1998). *Cell Death Diff. 5*: 461-468.
Smith and Jarrett (1988). *Laboratory Invest. 58*(6): 613-629.
Smith and Scott (1993). *Meth. Enzymol. 217*: 228-257.
Stephens, et al. (1997). *J. Autoimmunity 10*: 293-298.
Stephens, et al. (1999). *Endocrinol. 140*(7): 3219-3227.
Suzuki, et al. (2002). *J. Biol Chem. 277*(4): 2437-2443.
Terskikh, et al. (1997). *Proc. Natl. Acad. Sci. USA 94*: 1663-1668.
Thorens (1992). *Proc. Natl. Acad. Sci. USA 89*: 8641-8645.
Torgerson, et al. (1998). *J. Immunology 161*: 6084-6092.
Ulbrich, et al. (2000). *J. Controlled Rel. 64*: 63-79.
Usami, et al. (1998). *Biochem Pharmacol 55*: 185-191.
Wang, et al. (1999). *Endocrinol. 140*(3): 1200-1204.
Welsh, et al. (1999). *Mol. Med. 5*: 169-180.
Widmann, et al. (1995). *Biochem J. 315*: 203-214.
Yamada, et al (1999). *Diabetes 48*: 478-483.
Yoon, et al. (1999). *Science 284*: 1183-1187.
York, et al. (1999). *J. Biol Chem. 274*(2): 1164-1171.
Zacher, et al. (1980). *Gene 9*: 127-140.
Zeng, et al. (1996). *J. Peptide Sci. 2*: 66-72.
Zwick, et al. (1998). *Curr. Opin. Biotech. 9*: 427-436.
Pasquallini and Ruoslahti (1996). *Nature 380* 364-366.
Sela and Zisman (1997). *FASEB J. 11*: 449-456.
Volz, et al. (1995). *FEBS Letters 373*: 23-29.
Yamato, et al. (1997). *Horm. Metab. Res. 29*: 56-59.
Bonny, et al. (2000). *J. Biol. Chem. 275*(22): 16466-16472.
Hoorens, et al. (1996). *J. Clin. Invest. 98*(7): 1568-1574.
Bonny, et al. (1998). *J. Biol. Chem. 273*(4): 1843-1846.
Sela and Zisman (1997). *FASEB J. 11*: 449-456.
Gotoh, et al. (1987). *Transplantation 43*(5): 725-730.
Carithers and Lerner (1996). *Chem. Biol. 3*: 537-542.
Damke (1996). *FEBS Letters 389*: 48-51.
Hawiger (1999). *Current Opinion Chem. Biol. 3*: 89-94.
Avrameas, et al. (1998). *Proc. Natl. Acad. Sci. USA 95*: 5601-5606.
Rothbard, et al. (2000). *Nature Med. 6*(11): 1253-1257.
International Search Report for PCT/ IB01/ 02423. Mailed on Jul. 2, 2002.
International Search Report for PCT/IB03/03097, mailed Sep. 30, 2004.

INTRACELLULAR DELIVERY OF BIOLOGICAL EFFECTORS

This application is a continuation-in-part of U.S. Ser. No. 09/977,831, filed Oct. 15, 2001, and claims the benefit of U.S. Ser. No. 60/240,315, filed Oct. 13, 2000.

TECHNICAL FIELD OF THE INVENTION

The invention relates to the field of molecular biology.

BACKGROUND OF THE INVENTION

Techniques enabling the efficient transfer of a substance of interest from the external medium into cells, and particularly into cellular nuclei, are of considerable interest in the field of biotechnology. Such techniques may be useful for protein or peptide production, for regulation of gene expression, for analysis of intracellular signaling channels and for analysis of the effect of transporting a variety of different substances into a cell (or cell nucleus). Currently available techniques are often limited by the inability of a transfer vector to transfer biologically active substances into the cytoplasm (or nuclei) of cells in the host to be treated without affecting the host genome or altering the biological properties of the active substance.

Previously, transduction of large active substances into cells was limited by the size and biochemical properties of the substance being transported. However, recent progress in this field has been achieved with the use of transporter peptides or proteins. For example, Schwarze and colleagues described a 10-mer peptide derived from HIV, $TAT_{48-57}$, which is capable of transporting conjugated peptides or proteins intracellularly into tissues and across the blood-brain barrier. Schwarze et al., Science 285:1573 (1999). These conjugated peptides or proteins are thought to be internalized by cells via a protein transduction process that does not involve endocytosis. This discovery opened a new methodology for biomedical research and for direct delivery of drugs into patients. However, one important limitation of this approach is the lack of cellular specificity for these types of transporters. Thus, adverse side effects from interaction with normal, non-target tissues limit the usefulness of many of these non-specific transporter peptides. Such a limitation is particularly problematic in the treatment of chronic diseases such as diabetes.

A need remains in the art for an efficient, safe compositions and methods for specifically targeting various cell types for the intracellular delivery of drugs and therapeutic agents via peptide transport.

SUMMARY OF THE INVENTION

The present invention provides transporter peptides which are capable of translocating across a biological membrane. The invention also relates to methods of using such transporter peptides to translocate an effector across a biological membrane. The transporter peptides can be monomeric or multimeric.

In one aspect, the invention involves transporter peptides having at least one amino acid sequence selected from: $(X_mRX_oRX_n)$; $(X_mRRRX_n)$; $(X_mRRXRX_n)$; and $(X_mRXRX_n)$, where X is a non-basic amino acid; m is an integer from zero to fourteen; n is an integer, independent of m, between zero and fourteen; o is an integer, independent of m and n, between zero and five; and wherein the transporter peptide is capable of translocating across a biological membrane.

In one embodiment, the invention provides a transporter peptide having the amino acid sequence R-X-X-R. In other embodiments, the invention provides a transporter peptide having an amino acid sequence of any one of SEQ ID NOS: 1–34. In various other embodiments, the transporter peptides are derived from protein convertase ligands. In still other embodiments, the transporter peptides are derived from protein convertase cleavage sites.

In another aspect, the invention involves multimeric transporter peptides including two, three, four, five, six, seven, eight or more monomeric transporter peptides wherein each monomeric transporter peptide has at least one amino acid sequence selected from: $(X_mRX_oRX_n)$; $(X_mRRRX_n)$; $(X_mRRXRX_n)$; and $(X_mRXRRXX_n)$, where X is a non-basic amino acid; m is an integer from zero to fourteen; n is an integer, independent of m, between zero and fourteen; o is an integer, independent of m and n, between zero and five; and wherein the transporter peptide is capable of translocating across a biological membrane. The individual monomeric transporter peptides within a multimeric transporter peptide can be the same or different.

In another embodiment, the invention provides a multimeric transporter peptide having the amino acid sequence R-X-X-R. In other embodiments, the invention provides a multimeric transporter peptide having an amino acid sequence of any one of SEQ ID NOS: 1–34. In various other embodiments, the multimeric transporter peptides are derived from protein convertase ligands. In still other embodiments, the multimeric transporter peptides are derived from protein convertase cleavage sites.

In some embodiments, the multimeric transporter peptides include a spacer moiety and a linker moiety. Preferably, the spacer moiety and linker moiety are flexible, amphiphilic, non-immunogenic and unsusceptible to proteases. The linker can be, for example, polyethylene glycol.

In other embodiments, the monomeric or polymeric transporter peptide can include a reporter group. As used herein, a "reporter group" is any group capable of detection. Non-limiting examples include radioactive isotopes, fluorescent moieties, phosphorescent moieties, chemiluminescent moieties, and quantum dots. Other reporter groups include biotin, cysteine, histidine, haemagglutinin, myc or flag tags.

In some embodiments, transport peptides of the invention are represented by Formula I:

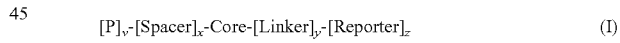

$$[P]_v\text{-}[Spacer]_x\text{-}Core\text{-}[Linker]_y\text{-}[Reporter]_z \qquad (I)$$

where P is a peptide, falling within the consensus motifs $(X_mRX_oRX_n)$; $(X_mRRRX_n)$; $(X_mRRXRX_n)$; and $(X_mRXRX_n)$, as described above. For example, the peptide can include the sequence $X_1\text{-}X_2\text{-}X_3\text{-}X_4$, where $X_1$ and $X_4$ can be R or K and $X_1$ and $X_4$ can be any amino acid. In one embodiment, the invention provides a multimeric transporter with at least one peptide having the amino acid sequence R-X-X-R. In other embodiments, the invention provides a multimeric transporter peptide with at least one peptide having an amino acid sequence of any one of SEQ ID NOS: 1–34. In various embodiments, the transporter peptides are derived from protein convertase ligands. In still other embodiments, the transporter peptides are derived from protein convertase cleavage sites. The number of peptides in a given transporter, represented by v, is an integer. In monomeric transporter, v is one. In a multimeric transporter, v is an integer from two to eight or more. In any given multimeric conjugate, each of the peptides may be the same as or different from each other.

In a monomeric transporter construct, the core may be present or absent.

A spacer may be present or absent between the peptide and core, thus x is either zero or one. Preferred spacers are flexible, amphiphilic, non-immunogenic and unsusceptible to proteases, and include polyethylene glycols (PEG) such as succinimidyl-PEG (succ-peg).

As used herein, a "core" is a structure that serves as an attachment point for linker, spacer, and reporter groups. The core also serves to connect the peptides within a multimeric transporter. In some embodiments, the core is branched so that many peptides can be attached in the same transporter unit. Typically, a core will have many functionalities available for attachment so that the various different moieties (the peptides and spacers, linkers, and reporter, if present) of the multimeric construct can be fused to the core, thereby generating one molecule. The contemplated core moieties include the polylysine (K) cores described in detail below and also include those structures having a built-in linker. The chosen core determines the number of peptides present within a given conjugate. Typical cores include: $C_4$-$K_2$K-K (succ-peg-S)-amide; C-GGG-[K(C)]$_3$-K(succ-peg-S)-amide; $(NH_2OCH_2CO)_4$-$K_2$K-K(succ-peg)-amide; $(NH_2OCH_2CO)_8$-$K_4K_2$K-K(GGG)-amide.

In the multimeric transporter construct, the linker and reporter groups can be present or absent, thus y and z are, independently, one or zero in Formula I.

As used herein, a "transporter peptide" is a peptide that facilitates the translocation of a substance across a biological membrane. Unless otherwise specified, or inaccurate in the context used, reference to a transporter peptide encompasses a monomeric or multimeric transporter peptide.

In some embodiments, the transporter peptide is fused to one or more effectors. The "effector" can be any suitable molecule, including DNA, RNA, a protein, a peptide, or a pharmaceutically active agent, such as, for example, a toxin, an antibiotic, an antipathogenic agent, an antigen, an antibody, an antibody fragment, an immunomodulator, an enzyme, or a therapeutic agent. When more than one effector is present, the effectors can be the same or different.

The term "fusion" or "fused" is meant to include all such specific interactions that result in two or more molecules showing a preference for one another relative to some third molecule. This includes processes such as covalent, ionic, hydrophobic, and hydrogen bonding, but does not include non-specific associations such as solvent preferences.

The multimeric conjugates of the invention can be represented by Formula (II):

  (II)

where P, Core, Spacer, Linker, Reporter, v, x, y, and z are as described above and E is an effector. In a covalently fused conjugate, the effector can be attached to the core, to the linker, or to both, as the laws of chemistry apply.

As used herein, "conjugate" or "conjugation" refer to any type of interaction enabling a physical association between an effector and a monomeric or multimeric transporter peptide. The association may be covalent or non-covalent in nature, and it must be sufficiently strong so that the conjugate does not disassociate before or during cellular translocation. Conjugation may be achieved using any chemical, biochemical, enzymatic or genetic coupling known to those skilled in the art. The effector of interest may be coupled or fused to the N-terminal or C-terminal end of the transporter peptide. In some embodiments, the effector is coupled or fused to a linker group, directly to the core, or to a reporter group.

In various embodiments, the monomeric and/or multimeric transporter peptides can be less than fifty (50), less than twenty-five (25), or less than fifteen (15) amino acids in length.

In further embodiments, translocation occurs within pancreatic B-cells, hepatocytes, colon cells, muscle cells and/or lung cells.

In another embodiment, the invention involves a method of translocating a transporter peptide across a biological membrane. For example, monomeric or multimeric peptides containing one or more of the sequences of SEQ ID NOS: 1–6 can be translocated across a membrane of pancreatic B-cells; monomeric or multimeric peptides containing one or more of the sequences of SEQ ID NOS: 7–10 can be translocated across a membrane of hepatocytes; monomeric or multimeric peptides containing one or more peptides of SEQ ID NO:11 can be translocated across a membrane of colon cells; monomeric or multimeric peptides containing one or more of the sequences of SEQ ID NOS: 12–20 can be translocated across a membrane of muscle cells; and monomeric or multimeric peptides containing one or more of the sequences of SEQ ID NOS: 21–34 can be translocated across a membrane of lung cells.

In yet another embodiment, the invention involves a transporter unit that is a monomeric or multimeric transporter peptide conjugated to one or more effectors. In various other embodiments, the effector may be a nucleic acid, a peptide, or a pharmaceutically active agent.

In still a further embodiment, the invention includes a method of producing a monomeric or multimeric translocatable conjugate between a transporter peptide and one or more effectors, thereby forming a transporter peptide-effector conjugate.

In another embodiment, the invention includes a method of translocating one or more effectors into the cytoplasm and/or nucleus of a eukaryotic cell, whereby the effector is conjugated to a monomeric or multimeric transporter peptide and introduced into the eukaryotic cell. For example, the transporter peptide-effector conjugate can be introduced into the cell by incubating a cell culture in the presence of the conjugate or by injecting the conjugate into the cell.

In various other embodiments, the invention includes a method of increasing the cellular concentration of an effector within a eukaryotic cell, whereby an effector is conjugated to a monomeric or multimeric transporter peptide and incubated in the presence of a cell under conditions promoting active metabolism of the cell. A preferred embodiment of the invention includes use of a human cell as the eukaryotic cell.

In further embodiments, the invention includes a pharmaceutical composition containing a therapeutically or prophylactically effective amount of a monomeric or multimeric transporter unit and a pharmaceutically acceptable carrier.

Preferred "pharmaceutical compositions" include tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

In yet still further embodiments, the invention includes a kit in which one or more containers containing a therapeutically or prophylactically effective amount of a pharmaceutical compositions of the invention.

Another embodiment of the invention involves a method of treating or preventing a disease by administering to a subject in which such treatment or prevention is desired, a pharmaceutical composition in an amount sufficient to treat or prevent a disease. For example, the disease to be treated may include diabetes, colon cancer, respiratory ailments, neurodegenerative disorders, cardioplegia, and/or viral infections.

In another aspect, the invention involves a method of screening a phage library for transporter peptides, whereby a phage library is screened against specific cell types and it is then determined which cells have internalised phages.

In another embodiment, this method includes identifying the DNA of an internalised phage and deducing an expressed peptide from this.

In yet a further embodiment, this method includes a screening step whereby a phage library is panned for at least three cycles.

In still a further embodiment, the invention includes a phage having a multivalent display of peptides.

DETAILED DESCRIPTION OF THE INVENTION

Figure 1:
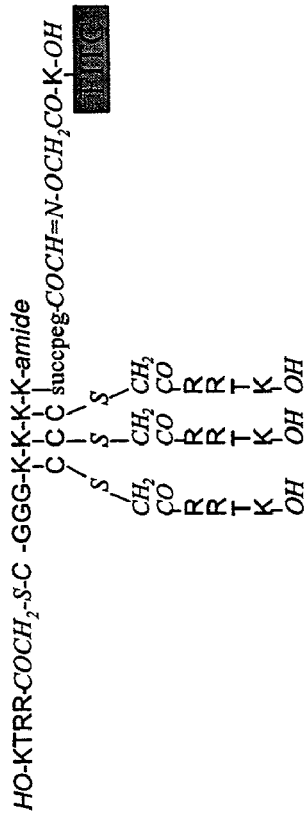
FIG. 1 shows the structures for oximes 1–3. The branching Lys residues of the cores are acylated on both alpha and epsilon amino groups with the N-terminus of RRTK peptide with or without a spacer. A reporter tag, FITC, together with a spacer is introduced into the core of each construct.
Figure 1:
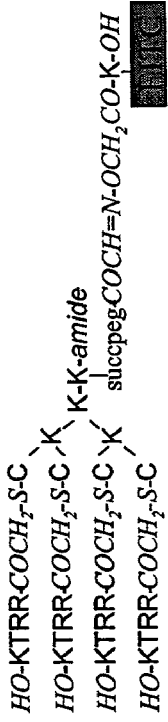
Figure 1:
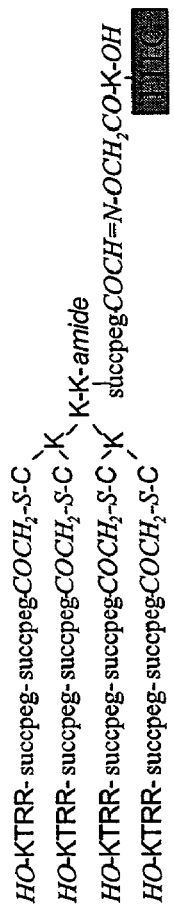

The present invention provides peptide transporters and a peptide transport system that specifically targets various cell types for the intracellular delivery of drugs and therapeutic agents. Existing transport systems known in the art are often limited because they are inefficient, affect the host genome, alter the biological properties of the active substance (e.g. the effector), kill the target cell, or pose too high a risk to be used in a human subject (e.g. due to the use of viral conjugates). The peptide transport system of the present invention uses proprotein convertases and specific ligands thereof for the intracellular delivery of potential therapeutics, in order to overcome the limitations of transport systems known in the art. The present system exhibits efficient delivery of an unaltered biologically active substance that does not affect the host's genome and that is otherwise non-invasive.

Receptor-mediated endocytosis has been widely exploited in experimental systems for the targeted delivery of therapeutic agents into cells. Kato and Sugiyama, Crit. Rev. Ther. Drug Carrier. Syst. 14:287 (1997). Thus, cell-type specific delivery of peptides may be achieved by successfully targeting cell specific endocytotic receptors. Proprotein convertases are one example of a cell surface receptor which gets internalized through receptor mediated endocytosis. These proteins have been shown to be responsible for conversion of precursors of peptide hormones, neuropeptides, and many other proteins into their biologically active forms. Cleavage sites for the proprotein convertase family contain the consensus R-X-X-R. Expression and localization information indicate that proprotein convertases transport extracellular ligands into the intracellular space.

For example, the mammalian proprotein convertases can be classified into three groups on the basis of their tissue distribution. In one class, Furin, PACE4, PC5/PC6, and LPCIPC7/PC8/SPC7 are expressed in a broad range of tissues and cell lines. In the second class, expression of the neuroendocrine-specific convertases PC2 and PC1/PC3 is limited to neuroendocrine tissues, such as pancreatic islets, pituitary, adrenal medulla and many brain areas. Further, in the third class, expression of PC4 is highly restricted to testicular spermatogenic cells. The neuroendocrine-specific convertases are mainly localized in secretory granules. PC5/PC6A has also been reported to be localized to secretory granules. Furthermore, indirect evidence has suggested that a proportion of proprotein convertases molecules is present on the cell surface, and it has been shown that furan cycles between the TGN and the cell surface. See Mandrup-Poulsen, BMJ. 316:1221 (1998).

Peptide ligands that mimic natural ligands are often identified using the phage display technique. The isolation of peptide sequences that direct efficient receptor-mediated endocytosis is enhanced by the use of phage display technologies. See Ivanenkov et al., Biochem. Biophys. Acta 1448:450 and 463 (1999). Phage display libraries are extremely powerful tools that provide for a vast source of molecular variants including modifications of natural ligands to cell receptors (Cabibbo et al., Gene 167:41 (1995)) and short peptides (Zwick et al., Curr. Opin. Biotechnol. 9:427 (1998)). Libraries have also been injected directly into mice where peptide sequences that show a 13-fold selectivity for brain and kidney have been successfully isolated. See Pasqualini and Ruoslahti, Nature 380:364 (1996); and Pasqualini and Ruoslahti, Mol. Psychiatry 1:423 (1996).

Occasionally, the ligands obtained by this procedure may be of low affinity (micromolar range) due to the high degree of conformational freedom and small number of contact residues within a short peptide molecule. One way to improve the binding affinity of peptide ligands is to combine several copies of the low-affinity peptides in a single multimeric molecule. Avidities (and bioactivities) of the multimeric ligand can be greatly enhanced relative to that of a monomeric ligand. In some embodiments, multimeric constructs are generated from cell-targeting peptides as building blocks using oxime chemistry. The peptides can be derived, for example, from phage display experiments which select for peptide ligands which bind specifically to particular cells (e.g., pancreatic β-cells) and are capable of eliciting uptake by these cells via receptor-mediated endocytosis.

For example, as a monomer, IgM is a low affinity protein, but, when in a pentameric form, its avidity is highly enhanced toward repetitive, antigenic determinants present on the surface of bacteria or viruses. See Roitt, Essential Immunology (Oxford/Blackwell, London), pp. 65–84 (1991).

Similarly, a $10^5$-fold enhancement occurred with the peptabody, a protein produced through recombinant DNA techniques. Alexey et al., Proc. Natl. Acad. Sci. USA 94:1663–1668 (1997). The low affinity of polypeptides derived from phage libraries is compensated by the pentameric structure of the peptabodies, resulting in high avidities towards their targets.

Recently, Rose also designed a similar a molecule named "chemobody". See Rose and Vizzavona, J. Am. Chem. Soc. 121:7034–7038 (1999). The chemobody is a synthetic molecule displaying multiple copies of a peptide subunit capable of binding non-covalently to a complementary structure, thus mimicking an antibody molecule. The amino acid sequence of the binding peptide was identified using phage library techniques and the subunits themselves were assembled using oxime chemistry. In order to be able to bind a target through two or more peptide subunits simultaneously, an appropriate spacer and a linker were also introduced into the chemobody. Rose generated a model chemobody having four copies of a phage-derived peptide from influenza virus with flexible linkers.

Small transporter peptides that selectively target specific cell types may be derived from large phage display libraries, and used as monomeric or multimeric transporter molecules. The advantages of small peptide carriers such as those obtained using phage display libraries include high quality and purity, low immunogenicity, and the potential for highly efficient delivery to all cells in an organism Schwarze et al., Science 285:1573 (1999). Accordingly, peptide carriers have the potential to improve upon conventional transporters such as liposomes or viruses for the efficient delivery of a variety of macromolecules. See, for example, Mahato et al., J. Drug Target. 4:337 (1997); and Mahato et al., Crit. Rev. Ther. Drug Carrier. Syst. 14:133 4:337 (1997).

The transporter peptides described herein have a use in treating a variety of diseases, including, but not limited to, diabetes. In a normal organism, β-cell mass is tightly regulated so that insulin secretion maintains normoglycemia. β-cell mass is adjusted in response to the needs of the infant or adult organism, in particular as a reaction to certain physiological and physiopathological conditions. The appropriate β-cell mass is essentially attained by a dynamic balance between β-cell death and regeneration. This balance is achieved by differentiation of immature β-cells and from the proliferation of preexisting insulin-secreting cells. See Scharfmann and Czernichow, Diabetes Metab. 22:223 (1996); and Bonner-Weir, Recent Prog. Horm. Res. 49:91 (1994). In Type I diabetes, impaired balance of β-cell mass results from as accelerated β-cell destruction, a process initiated by the specific attack of the immune system that targets pancreatic β-cells. Preventing or decreasing the rate of β-cell destruction may therefore not only help stabilize diabetes, but may also allow for islet regeneration to correct β-cell mass insufficiency.

Several compounds have been established as potent tools used to decrease the rate of β-cell loss in experimental models of Type I diabetes. Many of these molecules are peptidyl in nature, and thus are easily linked to peptide carriers. The peptides described herein serve as basis for the design of therapeutic "cargos", namely the coupling of the carriers (monomeric or multimeric "transporter peptides") with therapeutic agents ("effectors").

One embodiment of the transport system of the present invention targets β-cell intracellular mechanisms for the treatment of Type I diabetes. Symptoms of Type I diabetes are secondary to the destruction of the pancreatic β-cells by secretion of the immune system. See Mandrup-Poulsen, BMJ 316:1221 (1998). Conclusive data, both in human and rodents, indicates that the cytokine interleukin-1β (IL-1β) in conjunction with TNFα and IFNγ, secreted by macrophages and T-cells, are major components responsible for the final outcome that leads to β-cell dysfunction and destruction and Type I diabetes. See Mandrup-Poulsen, Diabetologia 39:1005 (1996); Nerup et al., Diabetes Care 11 Suppl 1:16 (1988); and Mauricio and Mandrup-Poulsen, Diabetes 47:1537 (1998). These secreted cytokines engage in a highly complex network of signaling and effector molecules in pancreatic β-cells. The signaling modifies the behavior of the cells and has a decisive impact on the cell fate. Accumulating evidence indicates that this regulatory intracellular network represents a promising target for the development of novel therapeutic approaches. See Iwahashi et al., Cytokines. Cell Mol. Ther. 4:45 (1998); Sjoholm, Cell Death. Differ. 5:461 (1998); Stephens et al., J. Autoimmun. 10:293 (1997); Rabinovitch et al., Diabetes 48:1223 (1999); Bleich et al., J. Clin. Invest. 103:1431 (1999); Welsh et al., Mol. Med. 5:169 (1999); and Chen et al., Diabetes 49:562 (2000). Each of the molecules involved in the treatment and integration of intracellular cytokine signaling may represent a target for transporter-drug design.

Among the most prominent signaling molecules recruited by IL-1β in β-cells are ceramides, prostaglandins, heat-shock proteins, the inducible NO synthase enzyme (iNOS), the transcription factor NF-κB (See Torgerson et al., J. Immunol. 161:6084 (1998)), and the three MAP kinases ERK1/2, p38 and JNK. Many of these molecules are targets for blockage with existing inhibitors that have led to improvement of β-cell survival and function. iNOS knock our (KO) mice are resistant to IL-1β cytotoxicity (See Flodstrom et al., Diabetes 48:706 (1999)) and blockers of iNOS activity prevent different aspects of NO cytotoxicity (reviewed in Sjoholm, Cell Death. Differ. 5:461 (1998)). Islets and cell-lines studies have indicated that blockers of $Ca^{2+}$ channels or caspase inhibitors prevent rodent β-cell death. See Wang et al., Endocrinology 140:1200 (1999); Yamada et al., Diabetes 48:478 (1999). p38 inhibitors attenuate IL-1β-mediated inhibition of glucose-stimulated insulin release. See Larsen et al., J. Biol. Chem. 273:15294 (1998). β-cell specific suppression of GAD expression in antisense GAD transgenic NOD mice prevented autoinimune diabetes. See Yoon et al., Science 284:1183 (1999). Expression of bcl-2, IL-1Ra as well as JBD (a dominant inhibitor of the c-Jun N-terminal Kinase JNK) in pancreatic β-cell lines has lead to the generation of cells that resist apoptosis. See Bonny et al., Diabetes 50:77–82 (2000); Iwahashi et al., Diabetologia 39:530 (1996); Dupraz et al., Gene Ther. 6:1160 (1999); and Giannoukakis et al., Diabetes 48:1730 (1999). Together, these data indicate that the manipulation of intracellular events with specific tools holds great promise for the treatment of Type I diabetes.

One major challenge for disease treatment is to convert biologically important molecules into bioactive, cell-permeable compounds which are usable in vivo. See Gibbs, Science 287:1969 (2000). For example, the most promising tools for the prevention of β-cell loss are a number of large proteins (e.g., Bcl-2 (See Rabinovitch et al., Diabetes 48:1223 (1999)), inhibitors of cytokine signaling such as dominant negative versions of MyD88, TRAF, FADD or IRAK (See Burns et al., J. Biol. Chem. 273:12203 (1998); and Stephens et al., Endocrinology 140:3219 (1999)), or the JNK inhibitor JBD280 (See Ammendrup et al., Diabetes 49:

1468–1476 (2000)) that cannot be currently delivered in vivo to tissues and cell-types including pancreatic β-cells.

Recent work indicates progress in attempts to convert large proteins into small bioactive compounds which can be easily delivered to cells and organs. See Hawiger, Curr. Opin. Chem. Biol. 3:89 (1999). These techniques essentially require two conditions: 1) a specific transporter or a chemical modification thereof is linked to the molecules for efficient delivery inside cells (see, for example, efficient short peptide transporters described in Schwarze et al., Science 285:1573 (1999); Brugidou, et al., Biochem. Biophys. Res. Commun. 214:685 (1995); Oehlke et al., Biochim. Biophys. Acta 1414:127 (1998); and Terskikh et al., Proc. Natl. Acad. Sci. U.S.A. 94:1663 (1997); and 2) the active portion of the protein has to be narrowed down so that small peptides sequence might be linked to the transporter. In short, these conditions generally define 3–30 amino acid long, bipartite peptides that are able to enter cells while conserving the essential biological properties of the proteins from which they are derived. As in cancer research (See Gibbs and Oliff, Cell 79:193 (1994)), there are numerous intracellular events in the β-cells whose manipulations protect β-cells from cytokine-induced apoptosis—manipulations which appear to be promising targets for drug design.

Receptor-mediated endocytosis is widely exploited in experimental systems for the targeted delivery of therapeutic agents into cells. See Kato and Sugiyama, Crit. Rev. Ther. Drug Carrier. Syst. 14:287 (1997). Endocytotic activity is a common property that has been described for many receptors including IgG Fc, somatostatin, insulin, IGF-I and II, transferrin, EGF, GLP-1, VLDL or integrin receptors. See Hofland et al., Proc. Assoc. Am. Physicians. 111:63 (1999); Anderson, Clin. Immunol. Immunopathol. 53:S63 (1989); Lund et al., J. Biol. Chem. 265:15713 (1990); Smith and Jarett, Lab. Invest. 58:613 (1988); Soler et al., Endocrinology 127:595 (1990); Widmann et al., Biochem. J. 310:203 (1995); York et al., J. Biol. Chem. 274:1164 (1999); and Mukherjee et al., Physiol. Rev. 77:759 (1997). Cell-type specific receptors that mediate endocytosis have been reported. See Ivanenkov et al., Biochem. Biophys. Acta 1448:463 (1999).

Although strong experimental background indicates that transporter peptides which selectively target pancreatic β-cells might be derived from large phage display libraries, no such attempts have been reported. The advantages of small peptide carriers such as those obtained using phage display libraries are numerous and include ease of generation by chemical synthesis, high quality and purity, low immunogenicity and potential for highly efficient delivery to all cells in an organism. See Schwarze et al., Science 285:1573 (1999). Accordingly, the peptide carriers of the invention have the potential to perform better than conventional transporters, such as liposomes or viruses, in the efficient delivery of many macromolecules. See, for example Mahato et al., J. Drug Target 4:337 (1997) and Mahato et al., Crit. Rev. Ther. Drug Carrier. Syst. 14:133 (1997).

Phage peptide libraries are traditionally constructed in derivatives of the filamentous phage M13. Peptide libraries are fused to the minor coat protein pIII of the capsid that displays 1–5 copies of the peptide motif. See Zwick et al., Curr. Opin. Biotechnol. 9:427 (1998). Alternatively, highvalent display is attained by using the major coat protein pVm. However, these types of libraries have not been optimized for the isolation of receptor-mediated endocytotic peptide sequences. The following considerations are relevant for the recovery of carriers with the highest efficiencies of internalization: 1) mono- or low-valent display of peptides is essentially insufficient for the efficient uptake of such large structures as filamentous phages, however multivalent display allows for efficient uptake (See Ivanenkov et al., Biochem. Biophys. Acta 1448:450 (1999)); and 2) the internalization of receptor-bound ligands involves concentration of cell surface receptors in specialized areas of the plasma membrane and subsequent formation of clathrin-coated vesicles (See Damke, FEBS Lett. 389:48 (1996)).

The large size of the M13 derivatives (1–1.5 μm) (See Zacher et al., Gene 9:127 (1980)) exceeds the typical size of classical clathrin-coated pits (150 nM). Clathrin-coated pits are invaginated structures on the plasma membrane that occupy approximately 2% of the membrane surface. These specialized structures direct the highly efficient receptor-mediated internalization process that clears extracellular proteins or peptides such as insulin or EGF at the extremely rapid rate of 10–50%/min. See Mukherjee et al., Physiol. Rev. 77:759 (1997). Thus, receptor-mediated internalization by these specialized and highly efficient structures is not expected to occur with the conventional M13 phages.

Accordingly, published attempts have failed to produce peptides that display a high internalization rate of peptide bearing phages. To date, no consensus internalization motif specific for a particular cell-type has emerged from these studies.

In certain aspects, the invention described herein relates to the identification of transporter peptides which promote the internalization of peptide-bearing effectors. Once the peptide sequences are determined, the peptides are bound to effector molecules in order to transport the effector molecules across a biological membrane. For example, a series of peptides that target pancreatic insulin secreting β cells were isolated by phage display panning. Monomeric and multimeric constructs employing these cell-targeting peptides as building blocks were synthesized. These constructs represent novel chemical entities designed to specifically deliver therapeutic agents to control diabetes.

Transport peptides of the invention can be represented by Formula I:

$$[P]_v\text{-}[Spacer]_x\text{-}Core\text{-}[Linker]_y\text{-}[Reporter]_z \qquad (I)$$

where P is a peptide, falling within the consensus motifs $(X_mRX_oRX_n)$; $(X_mRRRX_n)$; $(X_mRRXRX_n)$; and $(X_mRXR-RX_n)$, as described above. For example, the peptide can include the sequence $X_1\text{-}X_2\text{-}X_3\text{-}X_4$, where $X_1$ and $X_4$ can be R or K and $X_1$ and $X_4$ can be any amino acid. In one embodiment, the invention provides a multimeric transporter with at least one peptide having the amino acid sequence R-X-X-R. In other embodiments, the invention provides a multimeric transporter peptide with at least one peptide having an amino acid sequence of any one of SEQ ID NOS: 1–34. In various other embodiments, the transporter peptides are derived from protein convertase ligands. In still other embodiments, the transporter peptides are derived from protein convertase cleavage sites. The number of peptides in a given transporter, represented by v, is an integer. In monomeric transporter, v is one. In a multimeric transporter, v is an integer from two to eight or more. In any given multimeric conjugate, each of the peptides may be the same as or different from each other.

A spacer may be present or absent between the peptide and core, thus x is one or zero. Preferred spacers are flexible, amphiphilic, non-immunogenic and unsusceptible to proteases, and include polyethylene glycols (PEG) such as succinimidyl-PEG (succ-peg).

As used herein, a "core" is a structure that serves to connect the peptides within a multimeric transporter peptide. The core also serves as an attachment point for linker, spacer, and reporter groups. Typically, a core will have many functionalities available for attachment so that the various different moieties (the peptides and spacers, linkers, and reporter, if present) of the multimeric construct can be fused to the core, thereby generating one molecule. The core moieties contemplated include the polylysine (K) cores described in detail below and also include those structures having a built-in linker. The chosen core determines the number of peptides present within a given conjugate. Typical cores may include: $C_4$-$K_2$K-K(succ-peg-S)-amide; C-GGG-[K(C)]$_3$-K(succ-peg-S)-amide; $(NH_2OCH_2CO)_4$-$K_2$K-K(succ-peg)-amide; $(NH_2OCH_2CO)_8$-$K_4K_2$K-K (GGG)-amide. In a monomeric transporter peptide, the core may be present or absent.

In the transporter construct, the linker and reporter groups can be present or absent, thus y and z are, independently, one or zero in Formula I.

As used herein, a "transporter peptide" is a peptide that facilitates the translocation of a substance across a biological membrane. Unless otherwise specified, or inaccurate in the context used, reference to a transporter peptide encompasses a monomeric or multimeric transporter peptide.

A transporter peptide is a peptide that facilitates the passage, or translocation, of a substance across a biological membrane, particularly into the cytoplasm or nucleus, of the cell. Translocation may be detected by various procedures, including a cellular penetration assay as described in, for example, PCT application No. WO 97/02840. Generally, a cellular penetration assay is performed by: a) incubating a cell culture with a translocating peptide; b) fixing and permeabilizing the cells; and c) detection of the presence of the peptides inside the cell. The detection step may be carried out by incubating the fixed, permeabilized cells with labeled antibodies directed to the peptide, followed by detection of an immunological reaction between the peptide and the labeled antibody. Alternatively, detection may also be achieved by using a detectably labeled peptide, and directly detecting the presence of the label in cellular compartments. The label may be, for example, a radioactive label, or a fluorescent label, a dye, or any label capable of detection. See, e.g., de Jong et al., J. Nucl. Med. 40:2081 (1999); and Breeman et al., Int. J. Cancer 81:658 (1999).

The invention further includes transport units, or conjugates, which are complexes of the transporter peptide coupled or fused to an effector. As used herein, the term "coupled" means any type of interaction enabling a physical association between an effector and the peptide. The association may be covalent or a non-covalent in nature, and it must be sufficiently strong so that the vector does not disassociate before or during translocation. Coupling may be achieved using any chemical, biochemical, enzymatic or genetic coupling known to those skilled in the art. The effector of interest may be coupled to the N-terminal or C-terminal end of the peptide vector.

As used herein, the terms "fused" or "fusion" or "associates" or "interacts" are meant to include all specific interactions that result in two or more molecules showing a preference for one another relative to some third molecule, including processes such as covalent, ionic, hydrophobic, and hydrogen bonding, but does not include non-specific associations such as solvent preferences.

In some embodiments, the transporter peptide is coupled to or fused to one or more effectors. The coupling can be direct or can be through a core moiety. The "effector" can be any suitable molecule, including DNA, RNA, a protein, a peptide, or a pharmaceutically active agent, such as, for example, a toxin, an antibiotic, an antipathogenic agent, an antigen, an antibody, an antibody fragment, an immuno-modulator, an enzyme, or a therapeutic agent. When more than one effector is present, the effectors can be the same or different. An effector refers to any molecule or compound of, for example, biological, pharmaceutical, diagnosis, tracing, or food processing interest. Effectors may consist of nucleic acids (ribonucleic acid, deoxyribonucleic acid) from various origins, and particularly of human, viral, animal, eukaryotic or prokaryotic, plant, synthetic origin, etc. A nucleic acid of interest may be of a variety of sizes, ranging from, for example, a simple trace nucleotide to a genome fragment, or an entire genome. Likewise, it may be a viral genome or a plasmid. Alternatively, the effector of interest may also be a protein, such as, for example, an enzyme, a hormone, a cytokine, an apolipoprotein, a growth factor, an antigen, or an antibody, etc. Furthermore, the effector may be a pharmaceutically active agent, such as, for example, a toxin, a therapeutic agent, or an antipathogenic agent, such as an antibiotic, an antiviral, an antifungal, or an anti-parasitic agent. The effector of interest may itself be directly active or may be activated in situ by the peptide, by a distinct substance, or by environmental conditions.

The transporter peptide conjugates of the invention can be represented by Formula (I):

$$([P]_v\text{-}[Spacer]_x\text{-}Core\text{-}[Linker]_y\text{-}[Reporter]_z)\bullet E \qquad (II)$$

where P, Core, Spacer, Linker, Reporter, v, x, y, and z are as described above and E is an effector. In a covalently fused conjugate, the effector can be attached to the core, to the linker, or to both, as the laws of chemistry apply. In a monomeric transporter peptide conjugate (v=1), the core can be present or absent.

The term "pharmaceutically active agent" is used herein to refer to a chemical material or compound which, when administered to a human or animal organism induces a detectable pharmacologic and/or physiologic effect. The term "therapeutic agent" is used herein to refer to a chemical material or compound which, when administered to a human or animal organism induces a desired pharmacologic and/or physiologic effect.

The transporter peptides according to the present invention are characterized by the fact that their penetration capacity is virtually independent of the nature of the substance of the interest (the effector) that is coupled to it.

The invention also includes a method of introducing an substance of interest into a cell or a cell nucleus. The method includes contacting the cell with a transporter peptide-effector conjugate or transporter unit in an amount sufficient to enable efficient penetration into the cells. In general, the method may be used for in vivo or in vitro internalization of the conjugate. For example, the conjugate can be provided in vitro, ex vivo, or in vivo. Furthermore, a transporter peptide according to this invention may be capable of potentializing the biological activity of the coupled substance. Therefore, a transporter peptide can increase the biological activity of the effector to which it is coupled. In an in vitro method, an effector is coupled to a transporter, and the conjugate is incubated with cells at a temperature which enables active metabolism of the cells. In some cases, the transporter-effector conjugate is injected into particular cells. Those skilled in the art will recognize that any other method of introducing the conjugate into the cells can also be used.

In addition to the peptide-effector conjugates, the invention also provides a pharmaceutically acceptable base or acid addition salt, hydrate, ester, solvate, prodrug, metabolite, stereoisomer, or mixture thereof. The invention also includes pharmaceutical formulations comprising a peptide-effector conjugate in association with a pharmaceutically acceptable carrier, diluent, or excipient.

Salts encompassed within the term "pharmaceutically acceptable salts" refer to non-toxic salts of the compounds of this invention which are generally prepared by reacting the free base with a suitable organic or inorganic acid to produce "pharmaceutically-acceptable acid addition salts" of the compounds described herein. These compounds retain the biological effectiveness and properties of the free bases. Representative of such salts are the water-soluble and water-insoluble salts, such as the acetate, amsonate (4,4-diaminostilbene-2,2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

According to the methods of the invention, a human patient can be treated with a pharmacologically effective amount of a peptide or conjugate. The term "pharmacologically effective amount" means that amount of a drug or pharmaceutical agent (the effector) that will elicit the biological or medical response of a tissue, system, animal or human that is being sought by a researcher or clinician.

The invention also includes pharmaceutical compositions suitable for introducing an effector of interest into a cell or cell nucleus. The compositions are preferably suitable for internal use and include an effective amount of a pharmacologically active compound of the invention, alone or in combination, with one or more pharmaceutically acceptable carriers. The compounds are especially useful in that they have very low, if any, toxicity.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Administration of the active compounds and salts described herein can be via any of the accepted modes of administration for therapeutic agents. These methods include systemic or local administration such as oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active compound or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One approach for parenteral administration employs the implantation of a slow-release or sustained-released systems, which assures that a constant level of dosage is maintained, according to U.S. Pat. No. 3,710,795, incorporated herein by reference.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, may be provided in the form of scored tablets containing 0.5, 1.0, 2.5, 5.0, 10.0, 15.0, 25.0, 50.0, 100.0, 250.0, 500.0 or 1000.0 mg of active ingredient.

Compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Any of the above pharmaceutical compositions may contain 0.1–99%, preferably 1–70% of the active compounds, especially compounds of the Formula I as active ingredients.

Other Embodiments

The details of one or more embodiments of the invention have been set forth in the accompanying description above. From the foregoing detailed description of the specific embodiments of the invention, it should be apparent that unique methods and compositions for translocation across a biological membrane have been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims. For instance, the choice of the particular type of cell, or the particular effector to be translocated is believed to be a matter of routine for a person of ordinary skill in the art with knowledge of the embodiments described herein.

In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLES

Example I

Identification of Internalization Peptide Motifs

Phage peptide libraries are traditionally constructed in derivatives of the filamentous phage M13. Peptide libraries are fused to the minor coat protein pIII of the capsid that displays 1–5 copies of the peptide motif. See Zwick et al., Curr. Opin. Biotechnol. 9:427–436 (1998). Alternatively, high valent display is attained by using the major coat protein pVIII. These libraries however have not been optimized for the isolation of receptor-mediated endocytotic peptide sequences, because mono- or low-valent display of peptides is insufficient for efficient uptake of such giant structures as filamentous phages. Only a multivalent display allows for efficient uptake. See Ivanenkov et al., Biochim. Biophys. Acta 1448:450–462 (1999). In addition, the internalization of receptor-bound ligands involves concentration of cell surface receptors in specialized areas of the plasma membrane and subsequent formation of clathrin-coated vesicles (See Damke FEBS Lett. 389:48–51 (1996)), and receptor-mediated internalization by these specialized and highly efficient structures is not expected to occur with the conventional M13 phages.

Phage display libraries in the T7 415 phage system and in the T7 413b phage systems were constructed. This phage exhibits 415 copies of the displayed peptides within a reduced volume (capsid is ~50 nM diameter). Therefore, included in this invention is a phage display library in a novel phage system that fulfills the following criteria: multivalent display of 4-50-mer peptides (>400 copies/phage); small size (50 nM); efficient recovery of internalized phages;

removal of non-internalized bound-phages; and large number of individual peptide sequences ($3\times10^8$ independent clones, representing $>10^9$ heptapeptide sequences).

This library has been successfully used for the isolation of a peptide motif that directs efficient and specific intracellular delivery of macromolecules to the βTC-3 cell-model. In addition, this library has been used with five different (non-β-) cell lines, and in each case, the enrichment of peptide motifs specific for each cell-type has been observed. A general overview of the procedure is outlined below.

Selection/Enrichment Procedure

A phage display library is panned against a number of insulin-secreting cell-lines, rodent and human isolated islets and FACS purified β-cells, and finally is injected directly into animals (mice, rats, pigs) before extracting islets and recovering internalized phages. The panning procedure consists of at least three cycles of phage addition, recovery and amplification. Alternatively, and in order to isolate the most selective ligands, phages that bind other cell-types are subtracted by incubating the library with different non-insulin secreting cells before panning the library against β-cells. Experiments involving chloroquine to block lysosomal degradation are performed as described. See Ivanenkov et al., Biochem. Biophys. Acta 1448:450 (1999).

Determination of Phage Specificity

Panned phages are isolated and incubated with a number of different cells and organs. For example, in certain experiments, panned phages are incubated with insulin and non-insulin secreting cells and organs. Uptake is determined by counting the number of phages recovered. Immunocytochemistry studies are performed with anti-phage antibodies.

Characterization of Phage-beard Peptides

DNA from isolated phages are sequenced and expressed peptides are deduced. Peptides which direct internalization and mutated versions of these peptides are chemically synthesized and N-terminally labeled with FITC or iodinated. Labeled peptides are added to different cell types, isolated rodent and human islets, and directly injected into mice. Specificity of uptake, subcellular localization, clearance and stability are estimated. See Widmann et al., Biochem. J. 310:203 (1995).

Biochemical Assays

For analysis of insulin and non-insulin secreting cells, characterized peptides are linked to three known sequences: YVAD (caspases inhibitor, SEQ ID NO:35; Rouquet et al., Curr. Biol. 6:1192 (1996)), VQRKRQKLMP (inhibitor of NF-κB nuclear localization (Lin et al., J. Biol. Chem. 270:14255 (1995), SEQ ID NO:36) or RPKRPTTLNLF-PQVPRSQDT (JNK inhibitor, Bonny et al., Diabetes 50:77–82 (2000), SEQ ID NO:37). These peptides are chemically synthesized and added to insulin and non-insulin secreting cells. Caspases, NF-κB and JNK are activated by the general activator etoposide (See Kim et al., Anticancer Res. 20:439 (2000)) or anisomycin (See Usami et al., Biochem. Pharmacol. 55:185 (1998)). Inhibition of caspases, NF-κB and JNK by the peptides are studied in β- and non β-cells. These experiments indicate whether the peptide carriers transport potential drugs in an active conformation specifically inside the β-cells.

Uptake of Potential Therapeutic Agents by the GLP-1 Receptor

Expression of the GLP-1 receptor (GLP-1R) is mainly restricted to the brain and the pancreas. See Yamato et al., Horm. Metab. Res. 29:56 (1997). The receptor is internalized following binding to an agonist. See Widmann et al., Biochem. J. 310:203 (1995). These properties make the GLP-1R an attractive tool to mediate preferential delivery of therapeutic agents to the pancreatic β-cells. This property is evaluated as described above. Information gathered with the GLP-1R assists, for example, in the design of bispecific dimers with enhanced selectivity.

Identification of Other Internalization Motifs for the GLP-1 Receptor

COS-7 cells transfected with the GLP-1R serve as substrates for a panning experiments as above. Newly identified motifs are evaluated for their specificity and their capacity to direct endocytosis.

Production of All-D-retro-inverso Peptides

In some embodiments, the peptides can be synthesized as retro-inverso peptides. All-D-retro-inverso peptides with increased stability and lower immunogenicity (See Sela and Zisman, FASEB J. 11:449 (1997)) are analyzed as described above.

Evolution has ensured the almost exclusive occurrence of L-amino acids in naturally occurring proteins. Virtually all proteases therefore cleave peptide bonds between adjacent L-amino acids; thus, artificial proteins or peptides composed of D-amino acids are largely resistant to proteolytic breakdown. This resistance has been attractive to drug designers, but the exclusivity of biological systems for proteins made of L-amino acids means that such proteins cannot interact with the mirror image surface formed by enantiomeric proteins. Thus, an all D-amino acid protein usually has no biological effect or activity.

Linear modified retro-peptide structures have been studied for a long time (See Goodman et al., Accounts of Chemical Research, 12:1–7 (1979)) and the term "retro-isomer" was designated to include an isomer in which the direction of the sequence is reversed compared with the parent peptide. By "retro-inverso isomer" is meant an isomer of a linear peptide in which the direction of the sequence is reversed and the chirality of each amino acid residue is inverted; thus, there can be no end-group complementarity.

More recently, Jameson et al. engineered an analogue of the hairpin loop of the CD4 receptor by combining these two properties: reverse synthesis and a change in chirality. See Jameson et al., Nature 368:744–746 (1994) and Brady et al., Nature, 368:692–693 (1994). The net result of combining D-enantiomers and reverse synthesis is that the positions of carbonyl and amino groups in each amide bond are exchanged, while the position of the side-chain groups at each alpha carbon is preserved. Jameson et al. demonstrated an increase in biological activity for their reverse D peptide, which contrasts to the limited activity in vivo of its conventional all-L enantiomer (due to its susceptibility to proteolysis).

A partially modified retro-inverso pseudopeptide has been reported for use as a non-natural ligand for the human class I histocompatibility molecule, HLA-A2. See Guichard et al., Med. Chem. 39:2030–2039 (1996). Such non-natural ligands had increased stability and high MHC-binding capacity.

Retro-inverso peptides are prepared for peptides of known sequence in the following manner. A peptide having a known sequence (e.g., a tumor antigen peptide) is selected as a model peptide for designing and synthesizing a retro-inverso peptide analog. The analog is synthesized using D-amino acids by attaching the amino acids in a peptide chain such that the sequence of amino acids in the retro-inverso peptide analog is exactly opposite of that in the selected peptide which serves as the model. To illustrate, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art and are illustrated in the above-noted references.

Since an inherent problem with native peptides is degradation by natural proteases, the peptides of the invention may be prepared to include the "retro-inverso isomer" of the desired peptide. Protecting the peptide from natural proteolysis should therefore increase the effectiveness of the specific heterobivalent or heteromultivalent compound.

A higher biological activity is predicted for the retro-inverso containing peptide when compared to the non-retro-inverso containing analog owing to protection from degradation by native proteinases.

Production of Modified Peptides

In some embodiments, the peptides can be synthesized as modified peptides. The modified peptides are be analyzed as described above.

Analogs can differ from the native peptides by amino acid sequence, or by modifications which do not affect the sequence, or by both. Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the peptide's biological activity.

Modifications (which do not normally alter primary sequence) include in vivo or in vitro chemical derivitization of peptides, e.g., acetylation or carboxylation. Also included are modifications of glycosylation, e.g., those made by modifying the glycosylation patterns of a peptide during its synthesis and processing or in further processing steps, e.g., by exposing the peptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into peptides, are well known in the art. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

Production of Multimeric Peptides

Multimeric ligands display enhanced avidity of up to several orders of magnitude that translates in enhanced rate of internalization. See Terskikh et al., Proc. Natl. Acad. Sci. U.S.A. 94:1663 (1997); York et al., J. Biol. Chem. 274:1164 (1999). Monospecific dimers display great avidity and bispecific dimers are likely to have greater selectivity that may enhance their practical potential as specific cell-targeting agents. See Caruthers and Lerner, Chem. Biol. 3:537 (1996). Monomeric and multimeric peptides (both mono- and pluri-specific) can be synthesized as peptides or as peptidomimmetics, e.g., with either flexible peptidyl or sugar-based backbones. See Caruthers and Lerner, Chem. Biol. 3:537 (1996); Zeng et al., J. Pept. Sci. 2:66 (1996); Ulbrich et al., J. Controlled Release 64.(1.–3.):63.–79. 64:63 (2000).

Intracellular Localization

The different peptide sequences isolated may localize to different cell compartments (e.g., the nucleus, mitochondria, cytosol, etc.). This is evaluated using labeled (e.g., iodinated or FITC-labeled) peptides. This localization information is used for the design of the functional studies. For example, peptides accumulating in the cytosol are preferred for inhibiting NF-κB nuclear translocation, while peptides entering the nucleus are best suited for inhibiting JNK. In some embodiments, sequences such as nuclear localization motifs can be added to a conjugate to redirect the carriers to the appropriate cellular compartment.

Functional Studies

β-cell targeting transporter peptides (e.g., L- or D-enantiomers, monomeric or multimeric) linked to the caspase, NF-κB or JNK inhibitors are added to β-cell lines, FACS purified β-cells and isolated human and rodent islets. Apoptosis is induced by IL-β (in conjunction with TNFα and IFNγ) and resistance to apoptosis is evaluated.

In vivo Diabetes Experiments

NOD mice are injected in pre- and post-diabetic states with the effector peptides (β-cell targeting peptides linked to the caspase, NF-κB or JNK inhibitors). Dose and frequency of injection is determined as described above. Occurrence of diabetes is then measured.

Immunogenicity Assays

The immunogenic potential of the peptides is evaluated in rodents and rabbits.

Cloning

Peptide motifs that direct efficient uptake by specific cells are described in Examples III and IV. These peptides are used for the cloning and characterization of the cognate receptors from e.g., INS-1, βTC-3 and human islet cDNA libraries using established procedures. See Thorens, Proc. Natl. Acad. Sci. U.S.A. 89:8641 (1992); Volz et al., FEBS Lett. 373:23 (1995).

Characterization

Tissue distribution of the cloned receptor(s) is evaluated by Northern and Western blotting of insulin and non-insulin secreting cells and organs. Binding kinetics, clearance and specificity of uptake are evaluated by transient transfection of the receptors in COS-7 cells. Control peptides are mutated sequences as well as known peptides such as, for example, GLP-1, GIP, glucagon, secretin, etc. Alternative internalization motifs for these receptors are characterized by panning the library in transfected COS-7 cells as described above.

Example II

Methods of Screening for Transporter Peptides

Unless otherwise specified, all solvents and reagents were obtained from Fluka, Buchs, Switzerland, were of analytical or higher grade and were used without further purification. All amino acids were purchased from Peptide Institute Inc.(Japan). Resins were from Applied Biosystems, USA; Novabiochem, Switzerland, or Bachem, Switzerland. Water was repurified using a Milli-Q system (Millipore, Inc.). The insulin-secreting cell line βTC-3 was used in the bioassay. See Efrat et al., Proc. Natl. Acad. Sci. USA 85:9037–9041.

Phage Preparation and Enrichment Procedures

A library of 3×10⁸ independent phages displaying random 15-mer epitopes at the surface of the capsids was generated using standard procedures (e.g., in T7 415 or the T7 413b phage, Novagen). See Smith and Scott, Methods Enzymol. 217:228 (1993). Phages were amplified then purified by polyethylene glycol (PEG) precipitation and finally resuspended at a concentration of $10^{10}$ infective particles per μl in Tris-EDTA buffer (10:1 mM, TE) as described (by Smith and Scott, supra). Phages ($10^{12}$) were added to cells in culture medium for 1 to 24 hours. Longer incubation times were preferred to favor isolation of phages that escaped proteolytic degradation in endocytotic vesicles. Following binding and internalization, cells were washed and non-internalized phages were destroyed by digestion with subtilisin (3 mg/ml) (44). Following extensive washing, internalized phages were then recovered by lysing cells in a buffer containing 2% deoxycholate, 10 mM Tris-HCl and 2mM EDTA, pH 8.0. Recovered phages were finally amplified in *E. coli* cells (XL-1-Blue) and purified as described above. This preparation of selected phages was then used for a second round of panning. Three to five sequential rounds were performed to obtain enrichment of specific phage-bearing peptide sequences.

Immunocytochemistry and Fluorescence Studies

Single phages isolated according to the enrichment scheme above were amplified and added for 24 hours to cells in culture medium. Medium was then washed off and cells fixed in cold methanol-acetone (1:1) for 5 minutes. Antibodies directed against the phage capsid were used with a fluorescein-conjugated secondary antibody. Classical fluorescence microscopic studies and confocal microscopic assays were performed. Tissues were embedded in paraffin before processing.

Peptides

Peptides were synthesized using classical F-moc chemistry (Auspep, Australia), with a C-terminal amide group and labeled with FITC or iodinated when necessary. All peptides were purified by HPLC and analyzed by Mass-Spectrometry.

Biochemical Studies

Peptides are added one hour before JNK, NF-κB and caspases are activated in different cell-lines, such as, for example, βTC-3, INS-1, HeLa, WiDr, HepG2, NIH 3T3, COS-7, by etoposide (VP-16, Alexis) for 1 hour. Cell extracts are processed for JNK activity (using a solid phase JNK assay with c-Jun as substrate (See Bonny et al. J. Biol. Chem. 275:16466 (2000)), NF-κB nuclear translocation (electrophoretic mobility shift assay (See Lin et al., J. Biol. Chem. 270:14255 (1995)) and caspase activity (using available commercial kits and antibodies, Upstate Biochemicals).

Measurement of Apoptosis

Apoptosis is measured using a combination of Hoechst 33342 and propidium iodide as previously described. See Bonny et al., J. Biol. Chem. 275:16466 (2000); Hoorens et al., J. Clin. Invest. 98:1568 (1996).

Islets

Islets are isolated by the method of Gotoh et al. (Gotoh et al., Transplantation 43:725 (1987)). Human islets can be obtained, e.g., from the "Insel Spital", Bern, Switzerland.

Mice

The exact dosage and time-frame of injection is optimized for each peptide. However, previous experience with JNKI peptides indicates that 100 μl of a 1 mM solution of peptides in PBS injected every two days is a reasonable starting point.

λZASP-Express Library

The INS-1 cDNA library in the λZAP-Express prokaryotic/eukaryotic expression vector has been used to clone the IB1 and IB2 cDNAs. Bonny et al., J. Biol. Chem. 273:1843 (1998); Negri et al., Genomics 64:324 (2000). This library is easily converted to a plasmid library under the control of the eukaryotic CMV promoter by simple helper phage excision (Stratagene).

Example III

Panning of Phage Display Library and Characterization of Internalized Peptide Motifs The ability of specifically targeting β-cells for drug delivery will have an enormous impact on the treatment of Type I diabetes. Blockers of β-cell destruction that do not essentially alter β-cell function (i.e. insulin secretion) already exist (e.g. JBD, bc1-2). The conversion of one of these molecules (JBD) into a small peptide has been shown to retain full biological activity.

The pancreatic β-cell line βTC-3 was panned with the phage display library mentioned herein. Selective enrichment of the number of recovered phages was observed at each cycle of selection as seen below in Table 1. Panning experiments using βTC-3 cells were performed with $10^9$ phages used at each step of the enrichment procedure. The number of phages recovered at 0 ° C. (no endocytosis) is less than 100, indicating that the background of extracellular, but not internalized, bound phages is extremely low under the conditions described herein.

TABLE 1

| Panning | Phages recovered |
| --- | --- |
| 1ˢᵗ | <1 × 10³ |
| 2ⁿᵈ | 2 × 10⁵ |
| 3ʳᵈ | 3 × 10⁸ |

The occurrence of phages recovered after three steps of panning in the βTC-3 cell line is seen in Table 2.

TABLE 2

| P1 | 61% |
| --- | --- |
| P6 | 17% |
| P8 | 5.5% |
| P10 | 5.5% |
| P65 | 5.5% |
| P66 | 5.5% |

Titration experiments were performed with the phage P1 (SEQ ID NO:1) incubated with βTC-3 cells for the times indicated in Table 3. The ratio of input/recovered phages is also shown. Titration experiments indicated that as much as 10% of the initial P1 phage input could be recovered.

TABLE 3

| Phage | Incubation | % Recovered |
| --- | --- | --- |
| P1 | 1 h | 0.01 |
|  | 5 h | 1 |
|  | 17 h | 10 |

Determination of the specificity of uptake was performed by titrating the number of recovered phages in 5 different cell lines. Phages ($10^8$) were incubated for 16 hours with the indicated cell lines, and the number of internalized and recovered phages was calculated as seen in Table 4. Control phages displaying an integrin internalization motif showed a similar number (1–3×10$^6$) of recovered phages for all cell lines. This indicates that P1 (SEQ ID NO:1, see Table 5) is taken up by βTC-3 cells 10,000 to 1,000,000 fold more efficiently than by any other cell line tested.

TABLE 4

| Cells | Phages recovered |
| --- | --- |
| βTC-3 | 1 × 10$^7$ |
| HeLa | <1 × 10$^2$ |
| WiDr | 2 × 10$^2$ |
| HepG2 | <10 |
| A549 | 10$^3$ |

Peptides were then synthesized from the sequence of the displayed peptide in phage P1. The sequence of the P1 5-mer peptide was linked to a 10 amino-acid random sequence that was labeled with FITC. The control sequence was identical except that the P1 5-mer sequence was replaced by (Ala)$_5$. Peptides (10 μM) were added to the cells for one hour and cells were washed and fixed in cold methanol-acetone (1:1). FITC-labeled P1 peptides could be visualized inside βTC-3 cells, but not in other cell types.

Sequence analysis of 20 recovered phages at the final cycle of enrichment is shown in Table 5. Importantly, all sequences strictly obeyed to a same conserved consensus sequence of 5 amino acids. This suggests the specific selection/enrichment of a conserved motif that directs efficient uptake of the phages. A large proportion of the peptide motifs thus obtained obeys to the proprotein convertase consensus R-X-X-R. This observation forms the basis of the proposal to use proprotein convertases as vehicles for the intracellular delivery of potential drugs and macromolecules to specific cell-types.

TABLE 5

| | Cell Type | Sequence ID | Sequence | SEQ ID NO |
| --- | --- | --- | --- | --- |
| 1. | Pancreatic β-Cells | P1 | RRTK | 1 |
| 2. | | P6 | RKLR | 2 |
| 3. | | P66 | RRPK | 3 |
| 4. | | I2 | PTAKPTYTK | 4 |
| 5. | | I6 | IQGNGRQVGCLTNK | 5 |
| 6. | | I10 | MRGLSKRG | 6 |
| 7. | Hepatocytes | H2 | RQFRK | 7 |
| 8. | | H4 | RRIRG | 8 |
| 9. | | H6 | NRRRGIN | 9 |
| 10. | | H16 | KGKW | 10 |
| 11. | Colon Cancer | WP2 | RGNRGAR | 11 |
| 12. | Muscles | M1 | RRRR | 12 |
| 13. | | M2 | GRRKG | 13 |
| 14. | | M3 | ERRK | 14 |
| 15. | | M4 | SGGRKQR | 15 |
| 16. | | M6 | RSKR | 16 |
| 17. | | M7 | RRSGR | 17 |
| 18. | | M9 | KQRR | 18 |
| 19. | | M11 | GKRAR | 19 |
| 20. | | M13 | TGKRMTR | 20 |
| 21. | Lung | A2 | KRGR | 21 |
| 22. | | A3 | SLRRR | 22 |
| 23. | | A8 | PSLRRPR | 23 |
| 24. | | A10 | YKRGR | 24 |
| 25. | | A16 | GMGRKPR | 25 |
| 26. | | T1 | RRRVG | 26 |
| 27. | | T2 | RSFGVKKYG | 27 |
| 28. | | T3 | KSLRSFK | 28 |

TABLE 5-continued

| | Cell Type | Sequence ID | Sequence | SEQ ID NO |
| --- | --- | --- | --- | --- |
| 29. | | T5 | RVRR | 29 |
| 30. | | T7 | PRSRR | 30 |
| 31. | | T8 | MRRR | 31 |
| 32. | | T10 | YGGKRTLAMSK | 32 |
| 33. | | T11 | GRRSR | 33 |
| 34. | | T13 | YPLPNMK | 34 |

Example IV

Multimeric Conjugates

Ligand peptides obtained from phage library can be of low affinity (micromolar range). Their binding affinity or avidity may be enhanced by multimerizing copies of the peptide molecule, e.g., by generating a peptabody. See Scott and Smith, Science 249:386–90 (1990); Renschler et al., Proc. Natl. Acad. Sci. USA 91:3623–3627 (1994); Alexey et al., Proc. Natl. Acad. Sci. USA 94:1663–1668 (1997). Phage experiments indicated that the phage peptide RRTK (SEQ ID NO:1, see above) was taken up specifically by βTC-3 cells via receptor-mediated endocytosis, although the efficiency of internalization was low (which might be due to its low-affinity binding (approximately micromolar range). A series of multimers (FIGS. 1 and 2) displaying multiple copies (four or eight) of this peptide along with a reporter tag (either FITC or biotin) was constructed.

Multimeric transport peptides of the invention can be represented by Formula I:

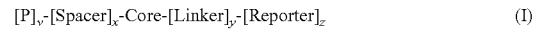

where P is a transporter peptide, such as the consensus motifs $(X_mRX_oRX_n)$; $(X_mRRRX_n)$; $(X_mRRXRX_n)$; and $(X_mRXRRX_n)$, as described above. For example, the peptide a peptide can include the sequence $X_1$-$X_2$-$X_3X_4$, where $X_1$ and X4 can be R or K and $X_1$ and $X_4$ can be any amino acid. The number of peptides in a given transporter peptide, represented by v, is an integer from two to eight or more. In any given multimeric transporter peptide, each of the peptides may be the same as or different from each other. Preferred peptides include those listed in Table 5.

A spacer may be present or absent between the peptide and core, thus x is one or zero. Preferred spacers are flexible, amphiphilic, non-immunogenic and unsusceptible to proteases, and include polyethylene glycols (PEG) such as succinimidyl-PEG (succ-peg).

The core moieties contemplated include the polylysine (K) core described in Table 7 and include those structures having a built-in linker. The core chosen determines the number of peptides present within a given conjugate. Typical cores include: $C_4$-$K_2$K-K(succ-peg-S)-amide; C-GGG-[K(C)]$_3$-K(succ-peg-S)-amide; $(NH_2OCH_2CO)_4$-$K_2$K-K(succ-peg)-amide; $(NH_2OCH_2CO)_8$-$K_4K_2$K-K(GGG)-amide. The linker and reporter groups can be present or absent, thus y and z are, independently, one or zero in Formula I.

The linker can be present or absent (i.e., y is one or zero). Linkers include those moieties which connect a core to a reporter and can be, for example, succ-PEG or $NH_2OCH_2CO$-Lys.

The reporter group can be present or absent (z is one or zero). The reporter group is any group capable of detection.

Non-limiting examples include radioactive isotopes, fluorescent moieties, phosphorescent moieties, chemiluminescent moieties, and quantum dots. Other reporter groups include biotin, cysteine, histidine, haemagglutinin, myc or flag tags. A typical fluorescent reporter group used herein is FITC (fluorescein isothiocyanate).

Figure 2:
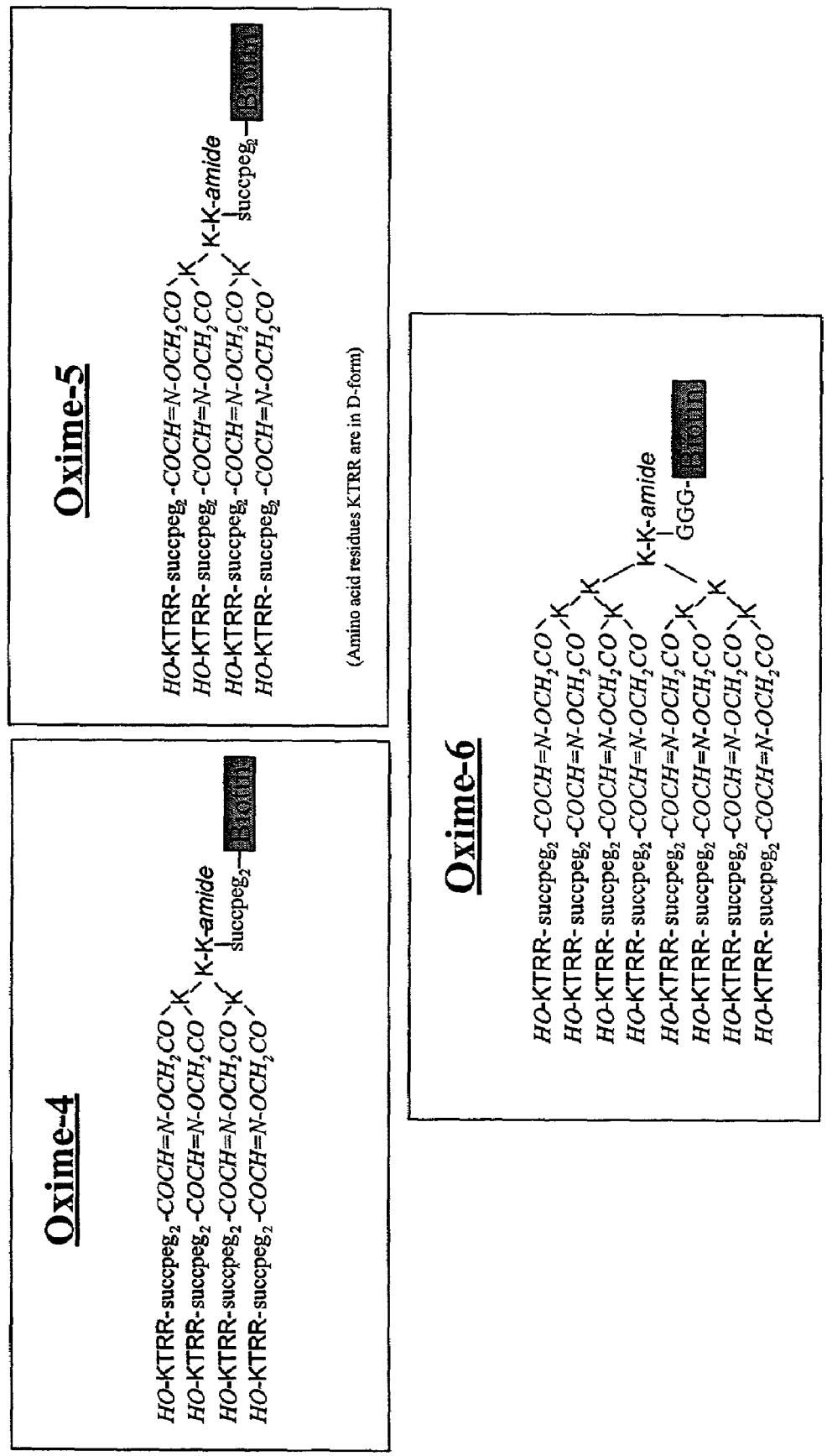
FIG. 2 shows the structures for oximes 4–6. The branching Lys residues of the cores are acylated on both alpha and epsilon amino groups with the N-terminus of RRTK peptide together with a spacer. A reporter tag, biotin, together with a spacer is introduced into the core of each construct.

Representative multimeric transporter peptides are shown in FIGS. 1 and 2.

In a multimeric transporter peptide unit or conjugate, the multimeric transporter peptide is fused to one or more effectors. The effector can be any suitable molecule, including DNA, RNA, a protein, a peptide, or a pharmaceutically active agent, such as, for example, a toxin, an antibiotic, an antipathogenic agent, an antigen, an antibody, an antibody fragment, an immunomodulator, an enzyme, or a therapeutic agent. When more than one effector is present, the effectors can be the same or different.

Thus, the multimeric conjugates of the invention can be represented by Formula (II):

([P]$_v$-[Spacer]$_x$-Core-[Linker]$_y$-[Reporter]$_z$)•E  (II)

where P, Core, Spacer, Linker, Reporter, v, x, y, and z are as described above and E is an effector. In a covalently fused conjugate, the effector can be attached to the core, to the linker, or to both, as allowed by the laws of chemical bonding.

Peptide Synthesis

The peptide sequence RRTK (P1, SEQ ID NO:1) was obtained from the phage display experiments that showed the peptide consensus motif X$_1$-X$_2$-X$_3$-X$_4$, where X$_1$ and X$_4$ can be R or K and X$_1$ and X$_4$ can be any amino acid, for binding to pancreatic β-cells. Peptides modified as seen in Table 6 were synthesized manually on 0.5 mmol Boc-Lys (CIZ)-PAM resin by Boc chemistry. Italic type denotes linker residues and space not present in the corresponding protein sequences. Several core structures used in this experiment are shown in Table 7. Synthesis was performed on 0.5 mmol methylbenzhydrylamine resin (MBHA resin) using Boc chemistry.

All peptides were cleaved from the resin with HF (0° C. for 1 h in the presence of 5% p-cresol), precipitated with cold ether, extracted with 50% acetonitrile, filtered, and lyophilized. The crude peptides were purified by preparative HPLC and characterized by ESIMS.

TABLE 6

Synthetic peptide sequences modified from RRTK (SEQ ID NO:1)

| Peptide 1 | BrCH$_2$CO-RRTK-OH |
| Peptide 2 | BrCH$_2$CO-(peg-succ)$_2$-RRTK-OH |
| Peptide 3 | H-S-(pog-succ)$_2$-RRTK-OH (L-form) |
| Peptide 4 | H-S-(pog-succ)$_2$-RRTK-OH (D-form) |

TABLE 7

Core structures used

| Core 1 | C$_4$-K$_2$K-K(succ-peg-S)-amide |
| Core 2 | C-GGG-[K(C)]$_3$-K(succ-peg-S)-amide |
| Core 3 | (NH$_2$OCH$_2$CO)$_4$-K$_2$K-K(succ-peg-Biotin)-amide |
| Core 4 | (NH$_2$OCH$_2$CO)$_8$-K$_4$K$_2$K-K(GGG-Biotin)-amide |

Preparation of a Fluorescein Linker

A fluorescein linker NH$_2$OCH$_2$CO-Lys(FITC)-OH was prepared according to Offord's method. See Offord, et al., Methods Enzymol. 287:348–69 (1997). In brief, 2 mmol of Boc-aminoxyacetyl (Boc-AOA-OSu) and 1.2 mmol of N$^\epsilon$-(TFA)-Lys were added into 3 ml of DMSO (dimethylsulfoxide) solution, and N-Ethylmorpholine was added until pH value 8–9. After incubation at room temperature for 15 hours and then at 37° C. for 1 hour, the pH value was brought to 3.0 by careful addition of glacial acetic acid under constant agitation. The product [Boc-AOA-Lys(TFA)-OH] was isolated on a preparative-scale HPLC and then dried. 4 ml water was added and then 0.44 ml piperidine (final concentration 1 M) into the dried compound, which was incubated 4 hours at room temperature, followed by pH adjustment to 3.0 on ice. The mixture was then diluted with 10 ml of 0.1% TFA. The deprotected material (Boc-AOA-Lys-OH) was isolated by preparative HPLC and dried again. The dried material was dissolved in 300 µl N,N-dimethyl-fomiamide (DMF), 40 mg fluorescein isothiocyanate (FITC) was added, and the mixture was adjusted to pH 8.0 with N-ethylmorpholine. After incubation for 15 hours in the dark, the product was purified by chromatography on a silica column [Kieselgel 60 (Fluka Chemie, Buchs, Switzerland), 1.5×20 cm] equilibrated in methanol/CH$_3$Cl (1:1, v/v). The excess FITC eluted in the flow-through fraction, and a second yellow fraction containing the expected product was eluted with methanol/CH$_3$-Cl (4:1, v/v). The solvent was removed by rotary evaporation, and the dried compound, Boc-AOA-Lys(FITC)-OH, was deprotected in TFA (at a concentration not exceeding 20 mg/ml) and left for 45 min at room temperature. The majority of the TFA was then evaporated and drying was completed by lyophilization. The final product [AOA-Lys(FITC)-OH] was isolated by preparative HPLC and characterized by ESI-MS.

Alkylation of Peptide Ligands to the Core 0.9 µmol of Cys-core peptide (1. 19 mg) was dissolved in 50 µl of acetonitrile and 100 µl of water (peptide not fully soluble). A fresh solution of bromoacetyl-peptide was prepared (3.6 µmol in 0.1M sodium phosphate buffer, pH 7.0). Then the alkylation was started by mixing two solutions at room temperature in dark. After 40 min, the product was purified on semi-preparative RP-HPLC, lyophilized, and characterized.

Periodate Oxidation

For periodate oxidation, 0.375 µmol of peptide (peptides 3 or 4 from Table 6, or the alkylated peptides listed in Table 8) was dissolved in 433 µl acetonitrile and 1.26 ml imidazole buffer (50 mM, pH 6.95, chloride counter ion). Methionine (113 µl, 200 mM) was added. Then 17 µl of NaO$_4$ (0.1 M in water) was added to start the oxidation. After 5 minutes, the reaction was quenched by adding 40 µl of ethylene glycol (500 mM in water). The product was purified on preparative HPLC and characterized by mass spectrometry.

TABLE 8

Alkylated peptides*

1 H-S-(peg-succ)$_2$-RRTK-OH
2 H-S-(peg-succ)$_2$-RRTK-OH (D-form)
3 [HO-KTRR-COCH2-S-C]$_4$-K$_2$K(succ-peg-S)-amide
4 [HO-KTRR-(succ-peg)$_2$-COCH$_2$-S-C]$_4$-K$_2$K(succ-peg-S)-amide
5 HO-KTRR-COCH$_2$-S-C-G3-[K(C-S-CH$_2$CO-RRTK-OH)]$_3$-K (succ-peg-S)-amide

*A bold letter denotes an amino acid residue.

Oximation

The aldehyde obtained by periodate oxidation was then reacted with core 3 or 4 (containing an AOA group in each core), or AOA-Lys(FITC)-OH, to form an oxime. Oximes 1–6, shown in FIGS. 1 and 2, were generated in this manner. The expected and found Mass Spec data are also provided in Table 9. As shown in FIG. 1, for oximes 1–3, the branching Lys residues of the cores were acylated on both alpha and epsilon amino groups with the N-terminus of RRTK (SEQ ID NO:1) peptide with or without a spacer. A reporter tag, FITC, together with a spacer was introduced into the core of each construct. In FIG. 2, oximes 4–6, the branching Lys residues of the cores were acylated on both alpha and epsilon amino groups with the N-terminus of RRTK(SEQ ID NO:1) peptide together with a spacer. A reporter tag, biotin, together with a spacer was introduced into the core of each construct.

TABLE 9

Oximes.

| Oxime | Expected Mass Spec | Found Mass Spec |
|---|---|---|
| Oxime 1 | 4289.04 | 4289.31 |
| Oxime 2 | 4460.18 | 4459.48 |
| Oxime 3 | 6708.00 | 6708.29 |
| Oxime 4 | 6160.3 | 6160.0 |
| Oxime 5 | 6160.3 | 6158.6 |
| Oxime 6 | 11643.6 | 11646.1 |

For oximations with AOALys(FITC)-OH, 0.129 μmol of oxidized construct was dissolved in 5 μl of acetonitrile and 200 μl of NaOAc buffer (acetic acid 0.57 ml in 100 ml of water, sodium acetate 0.82 g dissolved in 100 ml of water, mixed part of both until pH 4.0). 0.516 μmol AOA-Lys (FITC)-OH (8.8 mg/ml in 100 μl acetonitrile and 100 μl of NaOAc buffer) was added into the mixture, followed by addition of acetic acid to a final concentration of 4%. For oximation with core 3 or 4, 3.8 μmol of oxidized peptide 3 or 4 was dissolved in 100 μl of acetonitrile and 200 μl of NaOAc buffer. 0.475 μmol core 3 or 0.237 μmol core 4 was added into the solution, followed by addition of acetic acid to a final concentration of 4%. After 24 h reaction at room temperature, the product was purified on semi-preparative RP-BPLC and characterized by mass spectrometry.

Oxime 1 (FIG. 1) was constructed on a radial trilysine core (core 1) possessing a copy of RRTK (SEQ ID NO:1) peptide (peptide 1) at the end of each of 4 branches. Each peptide was N-terminally conjugated through a thioether bond arising from a specific reaction between bromoacetyl- and thiol-groups. The trilysine core also contained a succin-imidyl-PEG spacer and Serine capable of undergoing oxidation to generate an aldehyde, and thus the reporter group aminooxyacetyl-Lys(FITC) was introduced into the tetramer via oxime formation. HPLC and ESI-MS analysis revealed the desired product: Mass Spec data: Mr found 4289.31, Mr theoretical 4289.04. Oxime 1 was stable at acidic and neutral pH over 24 h.

Oximes 2 and 3 (FIG. 1) were similarly formed, however, on oxime 3 a two-unit PEG spacer was placed between the RRTK peptide (SEQ ID NO:1) and the core, and on oxime 2 the RRTK peptide (SEQ ID NO:1) was N-terminally conjugated to core 2 instead of core 1. Mass Spec data: oxime 2: Mr found 4459.48, Mr theoretical 4460.19; oxime 3: Mr found 6708.29, Mr theoretical 6708.00.

Oxime 4 (FIG. 2) was synthesized similarly to oxime 3, but a biotin group was attached directly via amide bond on the trilysine core, instead of using FITC group as a reporter. Mass Spec data: Mr found 6160.0, Mr theoretical 6160.3. oxime 5 was similar to Oxime 4, but the RRTK (SEQ ID NO:1) residues were all D-form. Mass Spec data: Mr found 6158.6, Mr theoretical 6160.3.

Oxime 6 was synthesized as oxime 4, but it contains eight copies of RRTK(SEQ ID NO:1) peptide instead of four copies. Mass Spec data: Mr found 11646.1, Mr theoretical 11643.6.

Immunocytochemistry and Fluorescence Studies

Single phages isolated according to the enrichment scheme above were amplified. The phage peptides and one of oximes 1–6 were added and incubated for 24 hours with cells in culture medium. Medium was then washed off and cells fixed in cold methanol-acetone (1:1) for 5 minutes. Antibodies directed against the phage capsid or against biotin (peptides) were used with a fluorescein-conjugated (phage) or Texas Red labeled (peptides) secondary antibody. Classical fluorescence microscopic studies and confocal microscopic assays were performed.

Oximes 1–3 were first tested for their entry into βTC-3 cells. Fluorescence studies showed that oxime 3, a tetraoxime (tree design) employing four copies of RRTK peptide with 2 units of PEG space as building blocks, clearly bound to the receptors on the surface of βTC-3 cells and was able to enter into the cells. The superiority of oxime 3 may be due to the flexibility of the PEG spacer, which increases binding to the receptors on the cells.

Oximes 4–6, which are similar to oxime 3, were then synthesized and assayed for binding avidity and entry efficiency. The number of copies of the RRTK(SEQ ID NO:1) peptide was increased up to eight in oxime 6, and, because D-peptides had been demonstrated to possess an increased stability and also lower immunogenicity (See Ivanenkov et al., Biochem. Biophys. Acta 1448:450 (1999)), the peptide was changed into its D-enantiomeric form in oxime 5. Microscopic examination showed that oxime 6, with eight copies of peptide (octaoxime), was able to efficiently enter cells. Texas Red labeled secondary antibody to the Biotin demonstrated that the octaoxime localized either inside cells as "vacuolar" structures, or at the cell membrane. Therefore, multimers where the peptide copy number is increased up to eight, exhibit enhanced avidity of the binding peptides and transport efficiency.

The invention claimed is:

1. A multimeric transporter peptide according to Formula I,

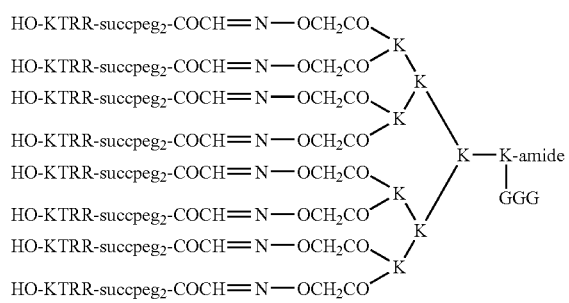

wherein said transporter peptide is capable of translocating across a biological membrane.

2. A transporter unit comprising the transporter peptide of claim 1 conjugated to an effector.

3. A transporter unit of Formula I:

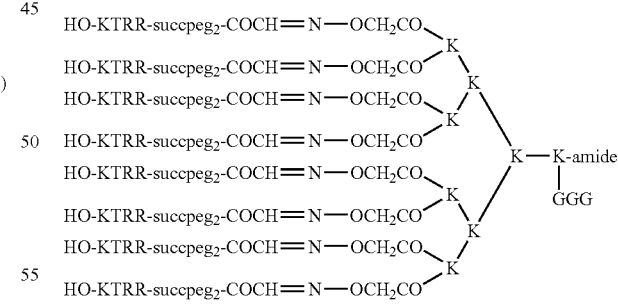

further comprising an effector that is a therapeutic agent; and wherein said transporter peptide is capable of translocating across a biological membrane.

4. The transporter unit of claim 3 wherein translocation occurs within pancreatic B-cells.

5. A pharmaceutical composition comprising a therapeutically or prophylactically effective amount of the transporter unit according to claim 3, and a pharmaceutically acceptable carner.

6. A kit comprising in one or more containers, a therapeutically or prophylactically effective amount of the pharmaceutical composition of claim 5.

7. A method of producing a translocatable conjugate between the transporter peptide of claim 1 and an effector, said method comprising conjugating said effector to said transporter peptide to form a transporter peptide-effector conjugate.

8. A method of translocating an effector into the cytoplasm and nucleus of a eukaryotic cell, said method comprising:
   conjugating said effector to the transporter peptide of claim 1 to form a transporter peptide-effector conjugate; and
   introducing said transporter peptide-effector conjugate to the cell.

9. The method of claim 8, wherein the introducing step is achieved by incubating a cell culture in the presence of said transporter peptide-effector conjugate or by injecting said transporter peptide-effector conjugate into the cell.

10. The method of claim 8, wherein the eukaryotic cell is a human cell.

11. The method of claim 8, wherein the eukaryotic cell is a β-cell.

12. A method of increasing the intracellular concentration of an effector within a eukaryotic cell, said method comprising;
   conjugating said effector to the transporter peptide of claim 1 to form a transporter peptide-effector conjugate;
   incubating said cell in the presence of said transporter peptide-effector conjugate, under conditions promoting active metabolism of said eukaryotic cell.

13. The method of claim 12, wherein the eukaryotic cell is a human cell.

\* \* \* \* \*

SEQUENCE LISTING

<160> NUMBER OF SEQ ID NOS: 37

<210> SEQ ID NO 1
<211> LENGTH: 4
<212> TYPE: PRT
<213> ORGANISM: Artificial Sequence

```
<220> FEATURE:
<223> OTHER INFORMATION: Description of Artificial Sequence: TRANSPORTER
      PEPTIDE

<400> SEQUENCE: 1

Arg Arg Thr Lys
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 2

Arg Lys Leu Arg
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 3

Arg Arg Pro Lys
  1

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 4

Pro Thr Ala Lys Pro Thr Tyr Thr Lys
  1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 5

Ile Gln Gly Asn Gly Arg Gln Val Gly Cys Leu Thr Asn Lys
  1               5                  10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 6

Met Arg Gly Leu Ser Lys Arg Gly
  1               5
```

```
<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 7

Arg Gln Phe Arg Lys
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 8

Arg Arg Ile Arg Gly
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 9

Asn Arg Arg Arg Gly Ile Asn
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 10

Lys Gly Lys Trp
 1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 11

Arg Gly Asn Arg Gly Ala Arg
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE
```

```
<400> SEQUENCE: 12

Arg Arg Pro Arg
 1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 13

Gly Arg Arg Lys Gly
 1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 14

Glu Arg Arg Lys
 1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 15

Ser Gly Gly Arg Lys Gln Arg
 1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 16

Arg Ser Lys Arg
 1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 17

Arg Arg Ser Gly Arg
 1               5

<210> SEQ ID NO 18
<211> LENGTH: 4
<212> TYPE: PRT
```

```
<213> ORGANISM: Artificial Sequence
<220> FEATURE:
<223> OTHER INFORMATION: Description of Artificial Sequence: TRANSPORTER
      PEPTIDE

<400> SEQUENCE: 18

Lys Gln Arg Arg
  1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 19

Gly Lys Arg Ala Arg
  1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 20

Thr Gly Lys Arg Met Thr Arg
  1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 21

Lys Arg Gly Arg
  1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 22

Ser Leu Arg Arg Arg
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 23

Pro Ser Leu Arg Arg Pro Arg
  1               5
```

```
<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 24

Tyr Lys Arg Gly Arg
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 25

Gly Met Gly Arg Lys Pro Arg
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 26

Arg Arg Arg Val Gly
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 27

Arg Ser Phe Gly Val Lys Lys Tyr Gly
 1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 28

Lys Ser Leu Arg Ser Phe Lys
 1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE
```

```
<400> SEQUENCE: 29

Arg Val Arg Arg
 1

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 30

Pro Arg Ser Arg Arg
 1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 31

Met Arg Arg Arg
 1

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 32

Tyr Gly Gly Lys Arg Thr Leu Ala Met Ser Lys
 1               5                  10

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 33

Gly Arg Arg Ser Arg
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 34

Tyr Pro Leu Pro Asn Met Lys
 1               5

<210> SEQ ID NO 35
<211> LENGTH: 4
```

```
<212> TYPE: PRT
<213> ORGANISM: Artificial Sequence
<220> FEATURE:
<223> OTHER INFORMATION: Description of Artificial Sequence: Caspase
      inhibitor peptide

<400> SEQUENCE: 35

Tyr Val Ala Asp
 1

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Inhibitor
      of NF-kB nuclear localization

<400> SEQUENCE: 36

Val Gln Arg Lys Arg Gln Lys Leu Met Pro
 1               5                  10

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: JNK
      Inhibitor

<400> SEQUENCE: 37

Arg Pro Lys Arg Pro Thr Thr Leu Asn Leu Phe Pro Gln Val Pro Arg
 1               5                  10                  15

Ser Gln Asp Thr
            20
```